(12) United States Patent
Schubert et al.

(10) Patent No.: US 7,427,510 B2
(45) Date of Patent: Sep. 23, 2008

(54) SYSTEM FOR PROCESSING SAMPLES IN A MULTICHAMBER ARRANGEMENT

(75) Inventors: Frank Ulrich Schubert, Munich (DE); Udo Eichenlaub, Penzberg (DE); Armin Tgetgel, Huglfing (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 626 days.

(21) Appl. No.: 11/189,201

(22) Filed: Jul. 25, 2005

(65) Prior Publication Data

US 2005/0281714 A1 Dec. 22, 2005

Related U.S. Application Data

(63) Continuation of application No. 09/738,385, filed on Dec. 16, 2000, now Pat. No. 6,921,513.

(30) Foreign Application Priority Data

Dec. 24, 1999 (DE) ................ 199 63 032

(51) Int. Cl.
  *G01N 1/10* (2006.01)
  *G01N 21/00* (2006.01)
(52) U.S. Cl. .............. 436/180; 436/174; 436/54; 422/100; 422/63; 422/65
(58) Field of Classification Search .......... 436/174, 436/180, 54; 422/99, 100, 63, 65; 222/566, 222/567, 570, 571
See application file for complete search history.

(56) References Cited

U.S. PATENT DOCUMENTS

| | | | |
|---|---|---|---|
| 3,785,773 A | 1/1974 | Rohrbaugh | |
| 3,912,456 A | 10/1975 | Young | |
| 4,167,875 A | 9/1979 | Meakin | |
| 4,287,155 A | 9/1981 | Tersteeg et al. | |
| 4,498,510 A * | 2/1985 | Minshew et al. | .............. 141/27 |
| 5,013,529 A | 5/1991 | Itoh | |
| 5,141,719 A | 8/1992 | Fernwood et al. | |
| 5,169,602 A | 12/1992 | Pang et al. | |
| 5,324,480 A | 6/1994 | Shumate et al. | |
| 5,330,439 A | 7/1994 | Jackson | |
| 5,707,589 A | 1/1998 | Fullemann | |
| 5,780,248 A | 7/1998 | Milchanoski et al. | |
| 5,842,582 A | 12/1998 | DeStefano | |
| 5,874,048 A | 2/1999 | Seto et al. | |

(Continued)

FOREIGN PATENT DOCUMENTS

EP  0407827  1/1991

(Continued)

*Primary Examiner*—Brian R. Gordon
(74) *Attorney, Agent, or Firm*—Townsend and Townsend and Crew LLP

(57) ABSTRACT

System for processing samples, in particular samples containing nucleic acids comprising a multichamber arrangement the chambers of which are used to receive liquids and it also concerns a pipetting device for removing liquids from the chambers and/or dispensing liquid into the chambers, wherein the system has a contamination protection which can move relative to the multichamber arrangement and which prevents contamination of an adjacent second chamber with liquid from the first chamber during a pipetting operation in the first chamber, by preventing discharge of fluid droplets from the first chamber into the second chamber by at least partially covering the first chamber.

10 Claims, 4 Drawing Sheets

U.S. PATENT DOCUMENTS

Figure 1:
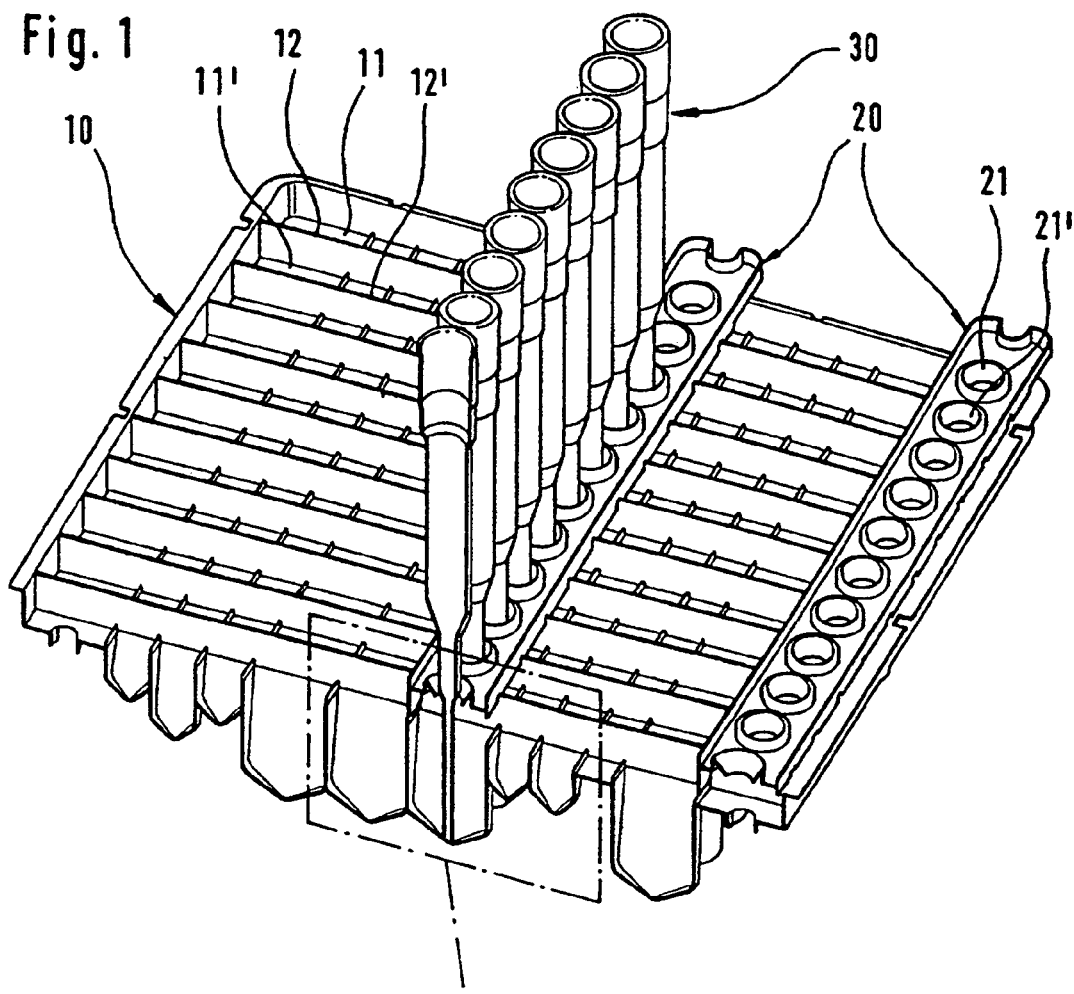

| | | | |
|---|---|---|---|
| 6,027,694 | A | 2/2000 | Boulton et al. |
| 6,251,686 | B1 | 6/2001 | Studer et al. |
| 6,326,212 | B1 | 12/2001 | Aoki |
| 6,464,943 | B1 | 10/2002 | Yiu |
| 6,500,390 | B1 | 12/2002 | Boulton et al. |
| 6,852,283 | B2 * | 2/2005 | Acosta et al. .................. 422/65 |
| 6,921,513 | B2 | 7/2005 | Schubert et al. |
| 2006/0172433 | A1 * | 8/2006 | Motadel ..................... 436/180 |
| 2006/0177942 | A1 * | 8/2006 | Matsubara et al. .......... 436/180 |

FOREIGN PATENT DOCUMENTS

| | | |
|---|---|---|
| EP | 0737110 | 10/1996 |
| EP | 0763739 | 3/1997 |
| EP | 0 843 176 | 5/1998 |
| EP | 0843176 | 5/1998 |
| EP | 0884104 | 12/1998 |
| JP | 59000638 | 1/1984 |
| WO | WO 91/17446 | 11/1991 |
| WO | WO 95/11083 | 4/1995 |
| WO | WO 97/03348 | 1/1997 |

* cited by examiner

SYSTEM FOR PROCESSING SAMPLES IN A MULTICHAMBER ARRANGEMENT

This is a continuation of U.S. application Ser. No. 09/738,385 now U.S. Pat. No. 6,921,513 filed Dec. 16, 2000.

The present invention is located in the field of sample processing in which the samples are processed in a multichamber arrangement in order to prepare the samples for later use and especially for analysis.

The invention concerns a system for processing samples with a multichamber arrangement the chambers of which are used to receive liquids and it also comprises a pipetting device for removing liquids from the chambers and/or dispensing liquid into the chambers, the system having a contamination protection which can move relative to the multichamber arrangement and which prevents contamination of an adjacent second chamber with liquid from a first chamber during a pipetting process in said first chamber. This is achieved by the contamination protection which prevents discharge of fluid droplets from the first chamber into the second chamber by at least partially covering or at least partially closing the first chamber.

The invention additionally concerns a process for processing samples with the aforementioned system and an application of the system to carry out a processing method.

For a long time it has been customary to take measures to prevent cross-contamination of liquids that are located in different chambers or containers during sample processing involving pipetting steps. For example disposable pipette tips are used for this which can be exchanged when a switch is made from processing a first liquid to processing a second liquid. Alternatively it is of course also known that a pipetting device can be cleaned by rinsing etc. when a switch is made from processing a first liquid to processing a second liquid. These measures are usually adequate for classical clinical automated analyzers. The increasing sensitivity of test methods and also the increasing miniaturization in this field with a concomitant pronounced reduction of the liquid volumes means that the transfer of minute amounts from one chamber into another chamber can already lead to considerable interference because subsequent analytical results are for example falsified. Especially during preparation of samples containing nucleic acids that are subjected to a subsequent amplification process, the transfer of an individual molecule of nucleic acid from one chamber into another chamber can already lead to a completely false analytical result. This can on the one hand be caused by the carry over of a positive sample from a first chamber into a negative sample in a second chamber which leads to a false-positive result for the sample in the second chamber. On the other hand liquid carry over can also generate false-negative results when for example an inhibitor of a detection reaction is transferred into a chamber.

It has now been found that contamination does not only occur by carry over from the pipetting device but also that droplets of liquid can be formed during the pipetting operations which spread as an aerosol and in this manner contaminate adjacent chambers or sample vessels. Hence such contamination cannot be prevented by washing the pipetting device or discarding a disposable pipetting device. In order to avoid contamination by aerosol formation it has already been attempted in the prior art to cover the individual chambers with slotted foils in which the pipetting device is introduced through the slit into the respective chamber. However, it has turned out that it is exactly such arrangements which promote aerosol formation since remnants of liquid from the pipette tip get onto the cover foil which starts to oscillate when the pipetting device is pulled out and hence generates an aerosol.

Precision System Science Ltd. took another approach to eliminating aerosol contamination by placing a multichamber arrangement in a system in which a laminar air current is directed such that aerosol that forms cannot reach adjacent chambers. Such an arrangement is described in the documents EP A 0 843 176 and EP A 0 763 739. However, the generation of a laminar air current requires quite an elaborate apparatus and in addition external disturbances can easily cause current turbulence in the laminar air.

The object of the present invention was to prevent adjacent chambers in which pipetting processes are carried out from being contaminated by aerosol carry over and to reduce contamination to such an extent that there is no interference of subsequent processes by the liquids. An additional object of the invention was to avoid contamination as simply and cost-effectively as possible and to influence or impede the processing steps as little as possible.

The said object was achieved by a system for processing samples as claimed in claim 1. In particular the system of the present invention provides a movable contamination protection which at least partially covers at least one of the chambers of the multichamber arrangement during a pipetting operation in this chamber.

The system of the present invention comprises firstly a multichamber arrangement in the chambers of which liquids are processed. Such multichamber arrangements are for example known from the above-mentioned patent document of the PSS Co. and from EP A 0 884 104. Multichamber arrangements for processing liquid samples are nowadays usually made of plastics such as polyethylene or polypropylene. However, multichamber arrangements made of other materials are also possible. The multichamber arrangement can be an arrangement of two or several connected chambers which are for example arranged in a row. In preferred embodiments the chambers are integrally connected together i.e. the multichamber arrangement is manufactured in one piece for example in an injection moulding process. However, the present invention is also intended to encompass such arrangements in which the chambers are separate and connected together by a holder or frame. The chambers of the multichamber arrangement are usually arranged in a row in order to enable a simple processing using conventional automated pipetting devices. On the other hand arrangements are of course also feasible which differ from such a linear arrangement. Furthermore the multichamber arrangement is not limited to just one row of chambers but rather it is even preferable that the multichamber arrangement has a two-dimensional arrangement of chambers.

The individual chambers are usually cylindrical and have a closed bottom. The top of the chambers are open and enable access to the chamber contents. The opening of each chamber is defined by the upper edge of the chamber. The planes in which these openings lie are preferably parallel to one another and are at the same height.

An important aspect of the present invention is the contamination protection which can move relative to the openings of the chambers. This means that, on the one hand, the contamination protection is moved whereas the multichamber arrangement is static or that, on the other hand, the contamination protection is stationary and the multichamber arrangement is moved. There are two basic designs for such a contamination protection. A common feature of both designs is that a movable contamination protection is provided which prevents aerosol discharge from a chamber in which pipetting is being carried out. This is achieved by designing the contamination protection, chamber and pipetting device such that the pipetting process itself takes place in a space that is extensively sealed against aerosol discharge.

In the first embodiment of the invention the contamination protection is attached to the pipetting device or directly to the pipetting needle and is thus moved together with the pipetting device. During the pipetting operations the pipette is lowered into the chambers and the contamination protection is also lowered onto the opening of the chamber in which pipetting occurs. Since the pipette may plunge into the chambers to different depths, the contamination protection may be designed such that it can slide along the axis of the pipetting needle. This can for example be an active, mechanically controlled movement or alternatively the contamination protection is spring-loaded relative to the pipetting device and is pressed by the spring onto the chamber opening when the pipette enters a chamber. In this first embodiment the contamination protection is moved by a movement of the pipetting device.

In a second embodiment of the invention the contamination protection is a separate part which is usually supplied with the multichamber arrangement. As described below in more detail in the description of the figures, the contamination protection can be a cover plate which is moved along the chambers. This cover plate is designed such that a pipetting needle can access the contents of a chamber while the chamber opening is covered by the cover plate in order to prevent aerosol discharge. The cover plate preferably has at least one opening through which the pipetting device or a pipetting needle can pass. The contamination protection is designed such that it essentially covers the opening of a chamber in which a processing step is carried out. In addition the dimensions of the contamination protection are such that only a small free cross-section of the chamber opening remains when the pipetting needle is in the chamber. In order to prevent the pipetting needle from being lowered onto the contamination protection which may occur as a result of tolerances, it is advantageous for the contamination protection to have an opening in the shape of a funnel which tapers towards the bottom. This ensures that the pipette tip finds its way into the chamber and that the remaining free cross-section of the chamber opening is only small when the pipette tip enters. In addition it is advantageous when the contamination protection does not just have a plane parallel plate shape but rather a three-dimensional structure which, in addition to a part which is arranged essentially parallel to the openings of the chambers, comprises a barrier arranged between the opening of the first and the second chamber when the contamination protection is located above the first opening. Such a barrier prevents aerosol from penetrating below the contamination protection from one chamber to another. The contamination protection and multichamber arrangement can also be advantageously designed such that they reversibly engage in positions in which the contamination protection is in each case located above a chamber or a row of chambers in such a manner that it prevents or at least reduces escape of aerosol from this chamber. Compared to the first basic embodiment of the invention, the second embodiment has the advantage that a plurality of chambers can be simultaneously protected from contamination in a simple manner. Furthermore special measures are not needed to enable different immersion depths of the pipetting needle or to ensure an optimal contamination protection for varying immersion depths.

When using the second embodiment of the invention it is advantageous when the pipette tip is not completely removed from the chamber or from the contamination protection between the pipetting operations. The pipette tip is preferably at the level of the contamination protection or somewhat lower to enable a common lateral movement of the pipette and contamination protection from a first chamber to a second chamber.

In order to coordinate the movement of the contamination protection with the pipetting operations, the system can have a separate movement device such as a robotic system to drive the contamination protection in one direction in space. Furthermore it is also possible to utilize the movement of the pipetting device to move the slidable contamination protection.

Pipetting devices are well-known in the prior art and thus only a cursory description is given here of their construction. Pipetting devices have a pipetting needle into which liquid is taken up in order to transport it, to remove it from a vessel or to dispense it into a vessel. The term needle refers to the shape of the pipetting needle which is usually a needle shape. The pipetting needle communicates with a pump such as a plunger sampler or a peristaltic pump in order to produce pressure differences in the pipetting needle for the pipetting operations. The pump is in turn connected to a control device to control the pipetting operations. Furthermore the pipetting device has a movement device in order to at least move the pipetting needle and optionally also a unit of pipetting needle and pump. The moving device moves the pipetting needle or the said unit relative to the multichamber arrangement. This comprises a lateral movement as well as a vertical movement to lower the pipetting needle into the processing chambers. The term pipetting device comprises a system of pipetting needle, pump, control device and moving device or a subcombination of the aforementioned units.

In addition a system according to the invention can have additional units e.g. for the analytical detection, to separate liquid components and to detect liquid levels. In particular the system can have units that are located in the area of the pipetting needle or are coupled to the pipetting needle (e.g. magnetic separation). These units are also protected from contamination by the contamination protection.

The processes for manipulating samples comprise numerous operations that are basically known in the prior art. For example lysing processes can be carried out with the samples in which an analyte is extracted from a carrier material. The most common process of this type in clinical analysis is lysis of cell material in order to release an analyte that may be present in the cell plasma or in the cell nucleus. Furthermore the processing can comprise purification processes in which the analyte is at least partially freed of other materials present in the sample. Such a purification process is of particular advantage in the field of nucleic acid analysis in order to avoid interference of the test by similar nucleic acids that may be present in a larger number. Such a purification process is preferably carried out by specifically binding the analyte to a solid phase e.g. glass beads on which oligonucleotides are immobilized to bind the analyte molecules by hybridization. Hence the processing also includes a so-called "bound free" separation in which the solid phase on which the analyte is located is separated from the liquid phase. A bound free separation can advantageously comprise the use of magnetizable beads which are held by applying a magnetic field while the liquid phase is separated. This separation can advantageously take place in the pipette tip as described in EP B 0 737 110. After the analyte has been separated on the solid phase, it is usual to carry out additional washing steps of the solid phase in which the particles are advantageously immobilized and resuspended in washing liquid to achieve a high washing efficiency. The washed solid phase is eluted after any washing steps i.e. the analyte is detached from the solid phase and transferred to the liquid phase. Moreover the liquid can also be processed in that chemical processes are carried out by adding reagents. The processed sample can now be directly analysed or in the case of nucleic acids an amplification can be carried out. However, processing in the sense of the present invention not only includes sample preparations for an analysis but also operations which for example result in a purified product for the production of a pharmaceutical preparation or such like. The above-mentioned processing steps are only meant as an illustration or to elucidate preferred embodiments. Hence the invention also includes other types of sample processing.

The present invention is now elucidated in more detail on the basis of several figures:

FIG. 1: Multichamber arrangement and contamination protection as well as pipette tips.

Figure 2A:
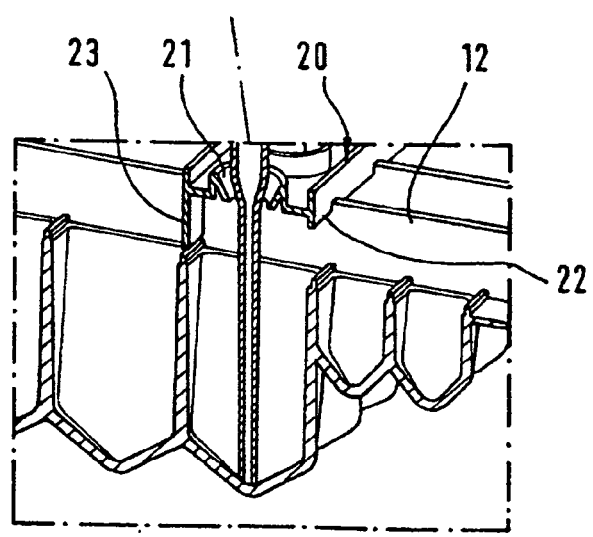
Figure 2B:
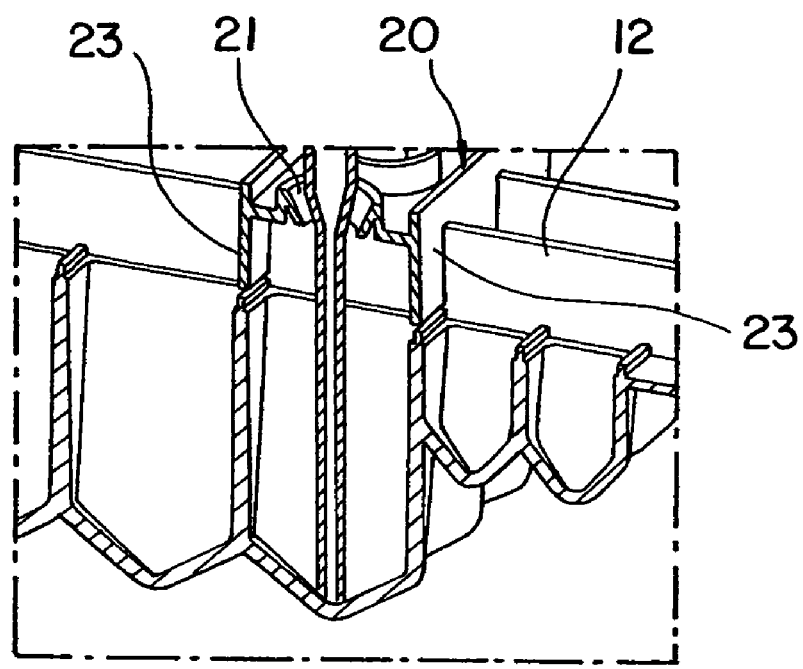

FIG. 2: Enlargement of a section of FIG. 1 comprising a chamber and its partial sealing by the contamination protection.

Figure 3:
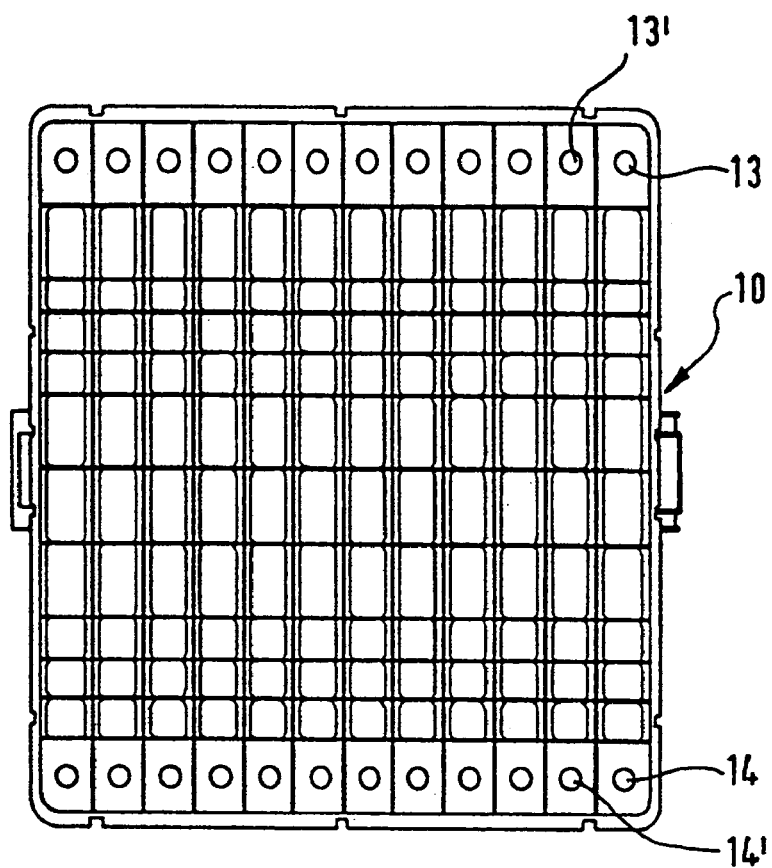

FIG. 3: Top view of a multichamber arrangement.

Figure 4:
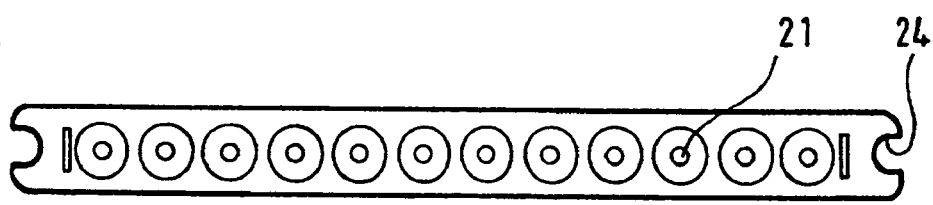

FIG. 4: Top view of the contamination protection.

Figure 5:
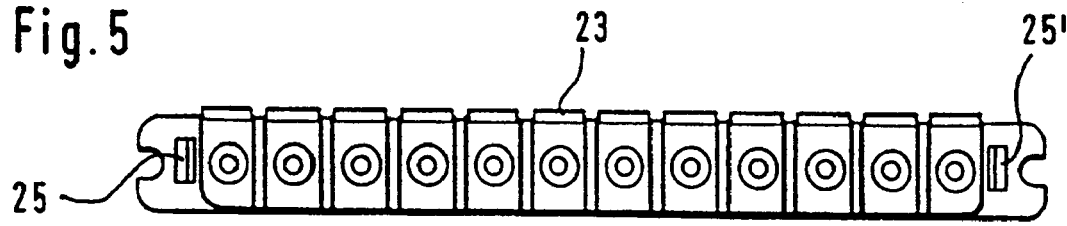

FIG. 5: Underside of the contamination protection of FIG. 4.

Figure 6:
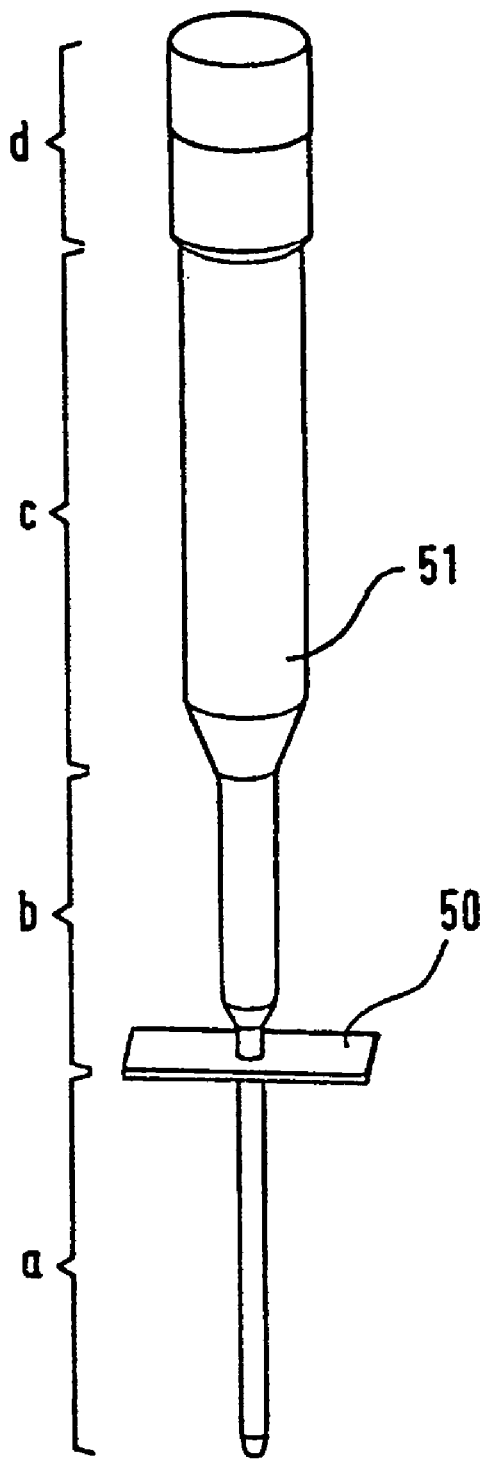

FIG. 6: Pipette with contamination protection.

FIG. 1 shows a perspective representation of a multichamber arrangement (10) and a contamination protection (20) which can be moved relative to the multichamber arrangement. FIG. 1 shows that the multichamber arrangement is composed of numerous chambers arranged in rows, several rows being adjacent to one another resulting in a two-dimensional array of chambers. In processes for sample preparation the sample is usually added first and this is processed in various steps during which liquid is transferred from one chamber into another chamber which is usually the adjacent chamber. In the arrangement of FIG. 1 the processing takes place concurrently in 10 rows. FIG. 1 additionally shows that the individual chambers in a row do not necessarily have the same holding capacity but rather that, depending on the process used, it may be advantageous to provide chambers of different sizes. FIG. 1 additionally shows that adjacent rows (11, 11') are separated from one another by crosspieces (12, 12'). These crosspieces represent a first protection to prevent transfer of liquid or aerosol from one row into an adjacent row. Furthermore the contamination protection (20) rests on these cross-pieces. Two elements for contamination protection (20) are illustrated in FIG. 1. However, in practice usually only one contamination protection is used. It can also be seen that the contamination protection has openings (21, 21') through which the pipette tips (30) are guided for the pipetting. It can be seen from FIG. 1 or even better from FIG. 2 that these openings have a funnel shape which tapers towards the bottom. This ensures that the pipette tip can be guided through the opening even when the positioning is not exact or in the case of component tolerances. Furthermore FIGS. 1 and 2 also show that the openings in the contamination protection are essentially closed by the pipettes such that essentially no aerosol can escape. In the case shown this is achieved by thickening the pipette tip in the area which comes to rest in the opening during the pipetting process. This is advantageous but not absolutely necessary. The contamination protection has a barrier (23) which is arranged essentially perpendicular to the opening of the vessels. This barrier is pulled down to such an extent that it almost extends to the level of the vessel openings. This forms a sort of chamber in which the pipetting process can take place and from which essentially no aerosol can escape into the subsequent chamber. Such barriers can be provided on both sides of the contamination protection. However, it is usually sufficient to provide a barrier only on the side in which the forward movement of the contamination protection occurs such that subsequent chambers in the processing are protected from contamination.

FIG. 3 shows a top view of the multichamber arrangement shown in FIG. 1. In addition to the features already mentioned it can be seen that the multichamber arrangement has openings (13, 13') which serve as set positions for separate vessels. This is advantageous for introducing a sample to be processed into the arrangement since it can be simply set in a holding position together with the vessel in which it is already located. Holding positions (14, 14') for a separate vessel which can receive the sample after processing are in turn located at the opposite side of the respective row of processing chambers. This facilitates transfer of the sample to be processed to other devices, especially thermocyclers or analytical devices, by removing the separate vessel.

FIG. 4 shows a top view of the separate contamination protection already shown in FIG. 1. In addition to the features already mentioned it can also be seen that both ends of the contamination protection have notches (24) into which guide elements of a moving device can engage in order to transport the contamination protection. The view of the underside of the contamination protection in FIG. 5 again shows the barriers (23) which prevent spread of the aerosol towards the later processing chambers. It can additionally be seen that the contamination protection has engaging elements (25) which are used to attach it to the edge of the multichamber arrangement in such a manner that it prevents a complete detachment of the contamination protection from the multichamber arrangement but still allows it to slide along the rows of chambers.

FIG. 6 shows a contamination protection according to a first embodiment of the invention. The contamination protection (50) is attached to the pipette (51). The arrangement shown can preferably be integrally manufactured in an injection moulding process. The contamination protection (50) is designed such that it substantially covers the opening of a chamber during a pipetting process in this chamber. The arrangement shown in FIG. 6 comprising a pipette and contamination protection can be used together with the multichamber arrangement shown in FIG. 3. The pipette shown in FIG. 6 has several thickness regions. Region (a) has a small cross-section to allow the pipette to be easily introduced into the openings. The thickness region (b) has a larger cross-section in order to take up large amounts of liquid and to achieve a reduced flow rate compared to region (a) during pipetting operations. This is favourable in order to carry out magnetic separations in this region since the risk of an undesired whirling up of the magnetic particles separated on the wall is low and it also ensures a complete penetration of a cross-section by a magnetic field. Region (c) has an even larger cross-section than region (b) in order to be able to take up adequately large amounts of liquid with the pipette. The region (d) is used to receive the disposable pipette tip by connection to a pipetting device.

The invention claimed is:

1. A method for processing samples in a system comprising
   a. a multichamber arrangement of chambers, each chamber comprising an opening for receiving liquids,
   b. a pipetting device for removing or dispensing liquid into the chambers; and
   c. a contamination protection comprising means for attaching the contamination protection to the multichamber arrangement such that the contamination protection is allowed to slide laterally relative to the multichamber arrangement, the contamination protection reducing contamination of two adjacent chambers with liquid from a first chamber during a pipetting operation in the first chamber by reducing discharge of liquid droplets from the first chamber into the two chambers adjacent to the first chamber by an at least partial covering of the first chamber;

the method comprising the steps of:
(1) performing a pipetting operation in the first chamber; and
(2) commonly laterally sliding the pipetting device and contamination protection relative to the multichamber arrangement to a second chamber.

2. The method as claimed in claim 1, wherein the contamination protection comprises two barriers in an essentially perpendicular orientation to the opening of the chambers on opposing sides of each opening.

3. The method as claimed in claim 1, in which the chambers are arranged in a row.

4. The method as claimed in claim 1, in which the contamination protection has a cover region which is arranged essentially parallel to the openings of the chambers when the contamination protection is arranged to reduce liquid discharge from the first chamber.

5. The method as claimed in claim 4, in which the surface dimensions of the cover region are such that it essentially completely covers the opening of a chamber below the cover region.

6. The method as claimed in claim 4, in which the cover region has at least one opening through which the tip of the pipetting device can be introduced into the chamber located below the cover region.

7. The method as claimed in claim 6, in which at least one opening in the cover region is conically tapered towards the chamber opening.

8. The method as claimed in claim 1, in which the multichamber arrangement has two or more lines of chambers arranged in a row.

9. The method as claimed in claim 1, wherein the method further comprises the step of keeping the tip of said pipetting device at the level of the contamination protection between the pipetting operations.

10. The method as claimed in claim 1, wherein the contamination protection and the multichamber arrangement can reversibly engage in positions in which the contamination protection is located above a chamber such that the escape of aerosol from the chamber is reduced.

* * * * *